(12) United States Patent
Mekalanos et al.

(10) Patent No.: US 6,254,874 B1
(45) Date of Patent: *Jul. 3, 2001

(54) ATTENUATED AUXOTROPHIC MICROORGANISMS HAVING A COMBINATION OF NON-ATTENUATING MUTATIONS AND METHOD FOR MAKING SAME

(75) Inventors: John J. Mekalanos, Cambridge; Karl E. Klose, Newton, both of MA (US)

(73) Assignee: President and Fellows of Harvard College, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/421,207

(22) Filed: Apr. 13, 1995

(51) Int. Cl.$^7$ ............. A61K 39/00; A61K 39/02; A61K 39/112; A01N 63/00

(52) U.S. Cl. ............. 424/234.1; 424/93.2; 424/93.4; 424/93.48; 424/258.1; 424/184.1; 435/69.3; 435/172.1; 435/172.3; 435/252.8; 435/252.33

(58) Field of Search .................... 424/93.2, 93.4, 424/93.48, 258.1, 184.1, 234.1; 435/69.3, 172.1, 172.3, 252.8, 252.33

(56) References Cited

U.S. PATENT DOCUMENTS

| | | | |
|---|---|---|---|
| 3,856,935 | 12/1974 | Germanier | 424/92 |
| 4,337,314 | 6/1982 | Oeschger et al. | 435/253 |
| 4,472,378 | 9/1984 | Shuster et al. | 424/92 |
| 4,503,036 | 3/1985 | Girardon et al. | 424/92 |
| 4,550,081 | 10/1985 | Stocker | 435/253 |
| 4,632,830 | 12/1986 | Formal et al. | 424/92 |
| 4,735,801 | 4/1988 | Stocker | 424/92 |
| 4,764,370 | 8/1988 | Fields et al. | 424/93 |
| 4,789,544 | 12/1988 | Nelson et al. | 424/92 |
| 4,837,151 | 6/1989 | Stocker | 435/172.3 |
| 5,077,044 | 12/1991 | Stocker | 424/92 |
| 5,079,165 | 1/1992 | Clements et al. | 435/252.8 |
| 5,110,588 | 5/1992 | Morona et al. | 424/92 |
| 5,162,226 | 11/1992 | Beachey et al. | 435/252.3 |
| 5,210,035 | 5/1993 | Stocker | 435/172.3 |
| 5,294,441 | 3/1994 | Curtiss, III | 424/93 |
| 5,527,529 | * 6/1996 | Dougan et al. | 424/258.1 |
| 5,547,664 | * 8/1996 | Charles et al. | 424/93.2 |

OTHER PUBLICATIONS

"Nitrogen Regulatory Locus "glnR" of Enteric Bacteria is Composed of Cistrons ntrB and ntrC: Identification of their protein products" by Nancy McFarland et al., Proc. Natl. Acad. Sci. USA 78(4):2135–2139 (1981).*

"Cloning and Complete Nucleotide Sequence of the Escherichia coli Glutamine Permease Operon (glnHPQ)" by Tsutomu Nohno et al., Mol. Gen. Genet. 205:260–269 (1986).*

"Expression of $\sigma^{54}$ (ntrA)–Dependent Genes Is Probably United by a Common Mechanism" by Sydney Kutstu et al., Microbiological Reviews 53(3):367–376 (1989).*

"Characterization of Mutations That Lie in the Promoter–Regulatory Region for glnA, the Structural Gene Encoding Glutamine Synthetase" by Linda McCarter et al., Mol. Gen. Genet. 197:150–160 (1984).*

"Evidence that Nitrogen Regulatory Gene ntrC of *Salmonella typhimurium* is Transcribed from the glnA Promoter as well as from a Separate ntr Promoter" by Krystyna Krajewska et al., Mol. Gen. Genet. 193:135–142 (1984).*

"A Sigma Factor and Auxiliary Proteins Required for Nitrogen–Regulated Transcription in Enteric Bacteria" by J. Keener et al., RNA Polymerase and the Regulation of Transcription.*

"Regulation of Transcription of glnA, the Structural Gene Encoding Glutamine Synthetase, in glnA:: Mu dl (Ap$^R$, lac) Fusion Strains of *Salmonella typhimurium*" by Krystyna Krajewska–Grynkiewicz et al., Mol. Gen. Genet. 192:187–197 (1983).*

"Role of Integration Host Factor in the Regulation of the glnHp2 Promoter of *Escherichia coli*" by Felix Claverie–Martin et al., Proc. Natl. Acad. Sci. USA 88:1631–1635 (1991).*

"Two Transcriptional Starts Sites Found in the Promoter Region of *Escherichia coli* Glutamine Permease Operon, glnHPQ" by T. Nohno et al., Nucleic Acids Research 15(6):2777 (1987).*

"A Binding Protein for Glutamine and Its Relation to Active Transport in *Escherichia coli*" by Joel H. Weiner et al., The Journal of Biological Chemistry 246(22):6933–6941 (1971).*

"Regulation of Glutamine Transport in *Escherichia coli*" by R.C. Willis et al., Journal of Bacteriology 122(3):1032–1037 (1975).*

"Nitrogen Control in *Salmonella typhimurium*: Co–Regulation of Synthesis of Glutamine Synthetase and Amino Acid Transport Systems" by S. Govons Kustu et al., Journal of Bacteriology 138(1):218–234 (1979).*

"The Regulation of Glutamine Transport and Glutamine Synthetase in *Salmonella typhimurium*" by P.R. Betteridge et al., Journal of General Microbiology 95:324–334 (1976).*

(List continued on next page.)

Primary Examiner—James C. Housel
Assistant Examiner—V. Ryan
(74) Attorney, Agent, or Firm—Hogan & Hartson LLP; Steven C. Petersen (57) ABSTRACT

A live non-virulent vaccine composition and method for preparing the same comprising a virulent microorganismal strain which contains at least two mutations, wherein the first mutation results in an auxotrophic mutant which requires for proliferation, a nutrient which is normally available in the host tissues in an amount required by the auxotrophic mutant for proliferation and the second mutation results in the inability of the auxotrophic mutant to specifically transport the required nutrient from host-tissues into the auxotrophic mutant thereby producing an attenuated strain.

57 Claims, 4 Drawing Sheets

OTHER PUBLICATIONS

"Construction of ΔaroA his Δpur Strains of *Salmonella typhi*" by Mary Frances Edwards et al., Journal of Bacteriology 170(9):3991–3995 (1988).*

"Clinical Acceptability and Immunogenicity of CVD 908 *Salmonella typhi* vaccine strain" by Carol O. Tacket et al., Vaccine 10(7):443–446 (1992).*

"Construction of Genetically Defined Double aro mutants of *Salmonella typhi*" by David M. Hone et al., Vaccine 9:810–816 (1991).*

"Comparison of the Safety and Immunogenicity of ΔaroC ΔaroD and Δcya Δcrp *Salmonella typhi* Strains in Adult Volunteers" by Carol O. Tacket et al., Infection and Immunity 60(2):536–541 (1992).*

"*Salmonella typhimurium* Loci Involved in Survival within Macrophages" by Andreas J. Bäumler et al., Infection and Immunity 62(5):1623–1630 (1994).*

"Intracellular Survival of Wild–Type *Salmonella typhimurium* and Macrophage–Sensitive Mutants in Diverse Populations of Macrophages" by Nancy A. Buchmeier et al., Infection and Immunity 57(1):1–7 (1989).*

"Genetic Control of the Innate Resistance of Mice to *Salmonella typhimurium*: Expression of the Ity Gene in Peritoneal and Splenic Macrophages Isolated in vitro" by Christopher R. Lissner et al., The Journal of Immunology 131(6): 3006–3013 (1983).*

"A Short History of Vaccination" by Susan L. Plotkin et al., *Vaccines* 1–7 (1988).*

"New Technologies for Making Vaccines" by Ronald W. Ellis, Ph.D., *Recombinant DNA Vaccines* 568–575.*

"Use of Attenuated Bacteria as Live Oral Vaccine Vectors" by John D. Clements et al., *Vaccine Research and Developments* 1:293–322 (1992).*

"Prokaryotic Transcriptional Enhancers" by David S. Weiss et al., Transcriptional Regulation 667–694 (1992).*

"Prokaryotic Transcriptional Enhancers and Enhancer–Binding Proteins" by Sydney Kustu et al., Trends in Biochemical Sciences 16(11):397–402 (1991).*

"Metabolism of *Mycobacterium tuberculosis*" by Paul R. Wheeler et al., *Tuberculosis: Pathogenesis, Protection, and Control* 353–385 (1994).*

"Ammonia Assimilation and Biosynthesis of Glutamine, Glutamate, Aspartate, Asparagine, L–Alanine, and D–Alanine" by Lawrence J. Reitzer et al., Section B. Class II Reactions: Conversion of Precursor Metabolites to Small–Molecule Building Blocks 302–320.*

"New Method for Generating Deletions and Gene Replacements in *Escherichia coli*" by Carol M. Hamilton et al., Journal of Bacteriology 171(9):4617–4622 (1989).*

Killian et al. Infection and Immunity 54(1):1–8, 1986.*

Kochan et al. Infection and Immunity 43(2):543–8, 1984.*

Webster II. New Riverside University Dictionary pp. 861 and 1290.*

Krajewska–Grynkiewicz et al. Mol. Gen Genet 192:187–197, 1983.*

Nohno et al. Mol. Gen Genet. 205:260–269, 1986.*

McFarland et al. Proc. Natl Acad Sci 78(4):2135–39, 1981.*

McCarter et al. Mol Gen Genet 197:150–160, 1984.*

Reitzer et al. "Ammonia Assimilation and Biosynthesis of Glutamine, Glutamate, Aspartate, Asparagine, L–Alanine and D–Alanine" In *Escherichia coli* and *Salmonella typhimurium*, Cellular and Molecular Biology, Section B. Class II Reactions: Conversion of Precursor Metabolites to Small–Molecule Building Blocks, 1987, pp. 302–320.*

McFarland et al. Proc. Natl Acad Sci 78(4): 2135–2139, 1981.*

Keener et al, "A Sigma Factor and Auxiliary Proteins Required for Nitrogen–regulated Transcription in Enteric Bacteria". In RNA Polymerase and the Regulation of Transcription, 1987, pp. 159–175.*

Nohno et al. Mol. Gen. Genet. 205:260–269, 1986.*

* cited by examiner

ATTENUATED AUXOTROPHIC MICROORGANISMS HAVING A COMBINATION OF NON-ATTENUATING MUTATIONS AND METHOD FOR MAKING SAME

This study was supported by NRSA award 1F32AI09118-01 (to K.E.K.) and National Institute of Health Grant AI 26289 (to J.J.M.), and has been assigned to the President and Fellows of Harvard College.

BACKGROUND OF THE INVENTION

1. Field of the Invention

The present invention relates to vaccines useful for the prevention or modification of microbial pathogenesis. In particular, this invention relates to vaccines comprising genetically attenuated microbial pathogens.

2. Description of the State of the Art

Microbial pathogens, or disease-producing microorganisms, can infect a host by one of several mechanisms. They may enter through a break in the skin, they may be introduced by vector transmission, or they may interact with a mucosal surface. Disease ensues following infection of the host, when the potential of the pathogen to disrupt normal bodily functions is fully expressed. Some disease-producing microorganisms possess properties, referred to as virulence factors, that enhance their pathogenicity and allow them to invade host or human tissues and disrupt normal bodily functions. The virulence of pathogens, that is, their ability to induce disease, depends in large part on two properties of the pathogen, invasiveness and toxigenicity. Invasiveness refers to the ability of the pathogen to invade host or human tissues, attach to cells, and multiply within the cells or tissues of the host. Toxigenicity refers to the ability of a pathogen to produce biochemicals, known as toxins, that disrupt the normal functions of cells or are generally destructive to cells and tissues.

The means by which vertebrates, particularly birds and mammals, overcome microbial pathogenesis is a complex process. Pathogens that invade the host provoke a number of incredibly versatile and protective systems. The first system that is triggered in response to tissue injury or infection is the complex defense mechanism of inflammation. Key to the inflammatory response is the release of various chemicals, such as histamine, from the injured tissue. Histamine causes blood vessels in the region to dilate, thus increasing local blood flow which results in swelling. The tissue fluid, which becomes loaded with extra clotting proteins from the plasma, begins to coagulate and prevents the normal flow of tissue fluid. As a result, the spread of the pathogen or its toxins is greatly slowed and is more or less confined to the area of tissue injury. In addition to this somewhat mechanical slowing of infection, the various chemicals that are released also serve to guide leukocytes or white blood cells toward the site of injury. The general function of leukocytes is to combat inflammation and infection. Some leukocytes, neutrophils and monocytes, are actively phagocytotic and they ingest microbial pathogens and other foreign material. Other leukocytes, lymphocytes, are key elements in the immune response of the body and are discussed in further detail below.

The rapidity of the inflammatory response is proportional to the extent of tissue destruction. Therefore, as an example, a staphylococcal infection, which produces great tissue destruction, is normally quickly confined by the inflammatory response, while streptococcal infections, which are less destructive, elicit a much slower inflammatory response. As a consequence, the confinement of Streptococcus and its toxins is less likely to be successful, and the pathogenic invasion can continue to spread throughout the body.

If all other barriers fail and the microbial pathogen or its toxins penetrate the body's defenses, as discussed above, and reach the bloodstream, the lymphoid tissue of the spleen, liver, and bone marrow will remove and destroy the foreign material as the blood circulates through these organs. Lymphoid tissue is composed primarily of a meshwork of interlocking reticular cells and fibers. Clinging to the interstices of the tissues are large numbers of leukocytes, more specifically lymphocyte cells, and other cells in various stages of differentiation, such as plasma cells, lymphoblasts, monocyte-macrophages, eosinophils and mast cells. The two main lymphocytes, T cells and B cells, have different and complementary roles in the mediation of the antigen-specific immune response.

The immune response is an exceedingly complex and valuable homeostatic mechanism having the ability to create antibodies against any foreign material or every chemical structure that might appear on the surface of a microbial pathogen or one of its toxic products. These foreign materials, referred to as antigens, elicit the ultimate response of the host, the acquired immune system, which operates by means of antibodies. An antibody is said to be specific as it attacks and binds only the antigen that triggered its production, thereby inactivating the antigen. The antigen contains some molecular species, usually protein or glycoprotein, that is not normally present in the host organism. Therefore, microorganismal cell membranes or toxins produced by the microorganism are considered antigenic in the host because they possess molecular species not normally present there.

The process of T cell and B cell development or differentiation describes the maturational events that begin with pluripotential bone marrow stem cells and end with a diverse population of specialized functioning T cells and B cells which mediate the cellular and humoral immune systems, respectively. In mammals, lymphocytes pass through the thymus gland in the throat where they differentiate into T cells, which mediate the cellular immune system. These cells are capable of killing other cells, and so this system is primarily effective against intracellular virus infections, fungi and parasitic worms. T cells also conduct an immune surveillance by watching the body's own cells for those that are developing into cancers. Other lymphocytes pass through the Peyer's patches, the small masses of lymphoid (lymphocyte-bearing) tissues that are distributed around the intestines, where they appear to differentiate into B cells. The B cells, through the production and release of antibodies (including secretory immunoglobulins of the secretory IgA subclass), which are a class of proteins known to mediate neutralization of extracellular bacteria and viruses.

There is a high degree of cooperation and interaction between these two classes of lymphocytes. T cells are first to detect the presence of antigens, and react quickly to bind the antigens with their surface receptor molecules. Once the antigen is bound, the T cell begins to proliferate by rapidly dividing and by producing the monomeric immunoglobulin that is localized on the membrane surface. The antigen-antibody (ag-ab) complexes that form as antigen molecules attach to these surface antibodies are released from the T cell and are then picked up by macrophage cells. The macrophage cells eventually become covered with ag-ab complexes that protrude from the surface with bound antigens facing away from the cells. The macrophage cells then present the antigens to B cells.

When a B cell binds to an antigen which has never been encountered, the cell undergoes repeated divisions to produce multiple clones. This event is considered a primary response. Within this population of "identical" cells, some mature to become antibody factories that release immunoglobulins into the blood. When they are fully mature, they become identified as plasma cells, cells that are capable of releasing about 2,000 identical antibody molecules per second until they die, generally within 2 or 3 days after reaching maturity. During the developmental changes, the plasma cells switch from producing general IgM type antibodies to producing highly specific IgG type antibodies. Other cells within this group of clones never produce antibodies but function as memory cells, which carry the program for the production of a highly specific IgG antibody that will recognize and bind a specific antibody.

Figure 1:
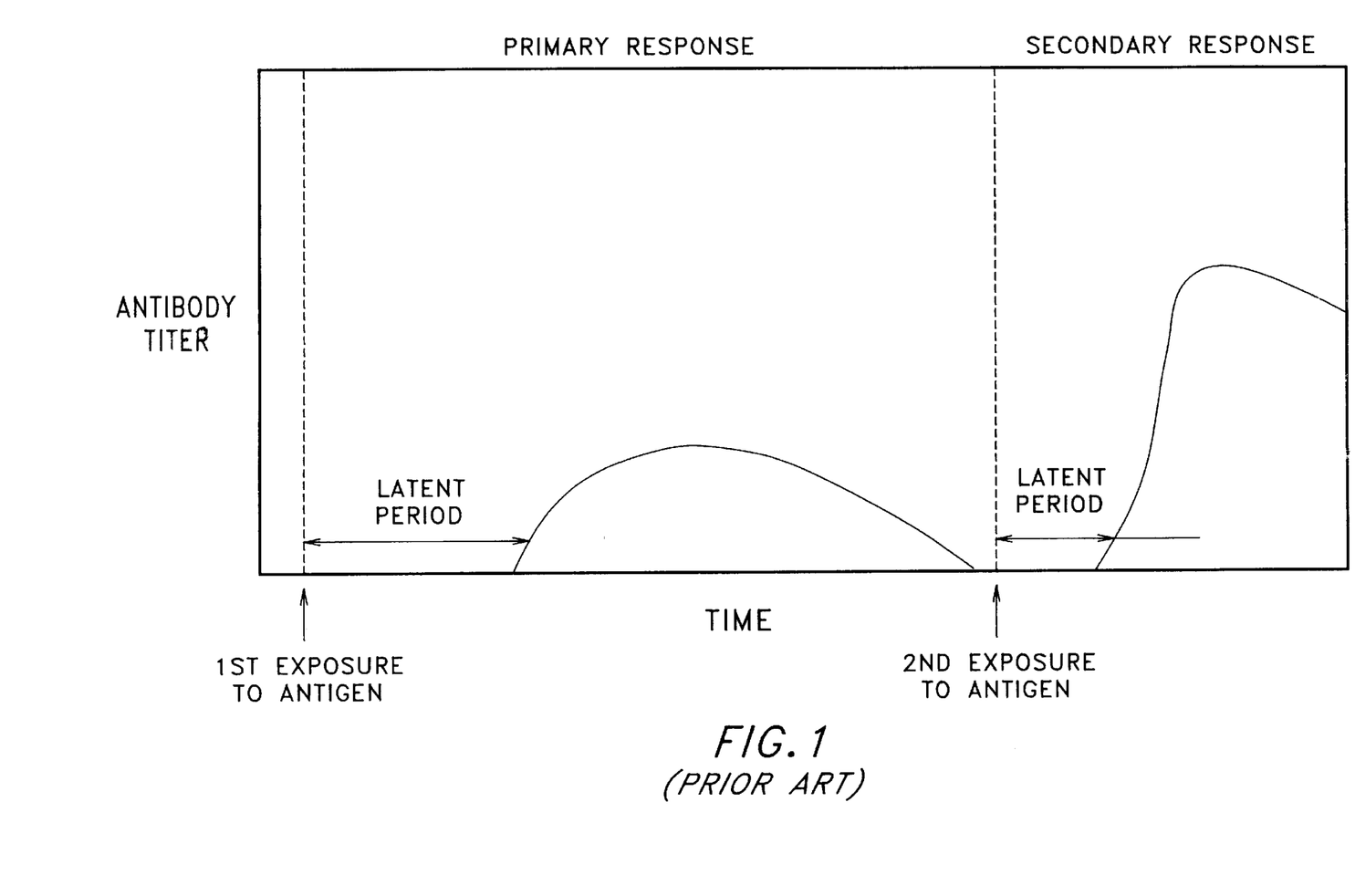
FIG. 1 is a graphic representation of the levels of antibody present following the primary and secondary immune responses.

As a consequence of the initial challenge by an antigen there are now many more cells identical to the original B cell or parent cell, each of which is able to respond in the same way to the antigen as the original B cell. Consequently, if the antigen appears a second time, it will encounter one of the correct B cells sooner, and since these B cells are programmed for the specific IgG antibody, the immune response will begin sooner, accelerate faster, be more specific and produce greater numbers of antibodies. This event is considered a secondary or amnestic response. FIG. 1 shows a comparison of the antibody titer present as a result of the primary and secondary responses. Immunity can persist for years because memory cells survive for months or years and also because the foreign material is sometimes reintroduced in minute doses that are sufficient to constantly trigger low-level immune responses. In this way the memory cells are periodically replenished.

Following the first exposure to an antigen the response is often slow to yield antibody and the amount of antibody produced is small, i.e., the primary response. On secondary challenge with the same antigen the response is more rapid and of greater magnitude, i.e., the secondary response. Achieving an immune state equal to the accelerated secondary response following reinfection with a pathogenic microorganism is the goal that is sought to be induced by vaccines. Vaccines are basically suspensions of viral, bacterial, or other pathogenic agents or their antigens which can be administered prophylactically to induce immunity.

Attempts to vaccinate are almost as old as man's attempts to rid himself of disease. However, during the last 200 years, since the time Edward Jenner deliberately and systematically inoculated a population with cowpox to avoid a smallpox epidemic, vaccination, at least in parts of the world, has controlled the following nine major diseases: smallpox, diphtheria, tetanus, yellow fever, pertussis, poliomyelitis, measles, mumps and rubella. In the case of smallpox, the disease has been totally eradicated from the world. The impact of vaccination on the health of the world's people is hard to exaggerate. With the exception of safer water, no other modality, not even antibiotics, has had such a major effect on mortality reduction and population growth.

In general, active vaccines can be divided into two general classes: subunit vaccines and whole organism vaccines. Subunit vaccines, are prepared from components of the whole organism and are usually developed in order to avoid the use of live organisms that may cause disease or to avoid the toxic components present in whole organism vaccines, as discussed in further detail below. The use of purified capsular polysaccharide material of *H. influenza* type b, as a vaccine against the meningitis caused by this organism in humans, is an example of a vaccine based upon an antigenic component. See Parks et al., *J. Inf. Dis.,* 136 (Suppl.):551 (1977), Anderson et al., *J. Inf. Dis.,* 136 (Suppl.):563 (1977); and Mäkela et al., *J. Inf. Dis.,* 136 (Suppl.):543 (1977).

Classically, subunit vaccines have been prepared by chemical inactivation of partially purified toxins, and hence have been called toxoids. Formaldehyde or glutaraldehyde have been the chemicals of choice to detoxify bacterial toxins. Both diphtheria and tetanus toxins have been successfully inactivated with formaldehyde resulting in a safe and effective toxoid vaccine which has been used for over 40 years to control diphtheria and tetanus. See, Pappenheimer, A. M., Diphtheria. In: *Bacterial Vaccines* (R. Germanier, ed.), Academic Press, Orlando, Fla., pp. 1–36 (1984); Bizzini, B., Tetanus. Id. at 37–68. Chemical toxoids, however, are not without undesirable properties. In fact, this type of vaccine can be more difficult to develop since protective antigens must first be identified and then procedures must be developed to efficiently isolate the antigens. Furthermore, in some cases, subunit vaccines do not elicit as strong an immune response as do whole organism vaccines due to the lack of extraneous materials such as membranes or endotoxins that may be more immunogenic due to the removal of materials that would otherwise mask the protective antigens or that are immunodominant.

Whole organism vaccines, on the other hand, make use of the entire organism for vaccination. The organism may be killed or alive (usually attenuated) depending upon the requirements to elicit protective immunity. The pertussis vaccine, for example, is a killed whole cell vaccine prepared by treatment of *Bordetella pertussis* cells with formaldehyde. The bacterium *B. pertussis* localizes in, and colonizes the epithelial lining of the respiratory tract resulting in a highly contagious respiratory disease, pertussis or whopping cough, of humans with morbidity and mortality rates highest for infants and young children. The colonization, further results in local tissue damage and systemic effects caused in large part by toxins produced by *B. pertussis. Manclarck et al., Pertussis. Id.* at 64–106. These toxins include endotoxin or lipopolysaccharide, a peptidoglycan fragment called tracheal cytotoxin, a heat-labile dermonecrotizing protein toxin, an adenylated cyclase toxin, and the protein exotoxin pertussis toxin. Vaccination is the most effective method for controlling pertussis, and killed whole-cell vaccines administered with diphtheria and tetanus toxoids (DPT vaccine) have been effective in controlling disease in many countries; Fine et al., Reflections on the Efficacy of Pertussis Vaccines, *Rev. Infect. Dis.,* 9:866–883 (1987). However, due to the large amounts of endogenous products, discussed above, contained in the vaccine many children experience adverse reactions upon injection. Endotoxin, which is an integral component of the outer membrane of the gram-negative organism (as well as all other gram-negative organisms) can induce a wide range of mild to severe side effects including fever, shock, leukocytosis, and abortion. While the side effects associated with pertussis vaccine usually are mild, they may be quite severe. The toxic components present in influenza virus vaccines, however, can induce a strong pyrogenic response and have been responsible for the production of Gufflain-Barré syndrome. Since influenza vaccines are prepared by growth of the virus in chick embryos, it is likely that components of the embryo or egg contributes to this toxicity.

The use of killed vaccines has also been described by Switzer et al., U.S. Pat. No. 4,016,253, who applied such a method in preparing a vaccine against *Bordetella bronchiseptica* infection in swine. In a technical paper by Brown et al., *Br. Med. J.*, 1:263 (1959), the use of killed whole cells is disclosed for preparing a vaccine against chronic bronchitis caused by *Haemophilus influenzae*. The use of killed cells, however, is usually accompanied by an attendant loss of immunogenic potential, since the process of killing usually destroys or alters many of the surface antigenic determinants necessary for induction of specific antibodies in the host.

In the case of intracellular pathogens, it is generally agreed that vaccines based on live but attenuated microorganisms (live vaccines) induce a highly effective type of immune response. Ideally, these attenuated microorganisms maintain the full integrity of cell-surface constituents necessary for specific antibody induction yet are unable to cause disease, because they fail to produce virulence factors, grow too slowly, or do not grow at all in the host. Additionally, these attenuated strains should have substantially no probability of reverting to a virulent wild-type strain. Traditionally, live vaccines have been obtained by either isolating an antigenically related virus from another species, by selecting attenuation through passage and adaptation in a nontargeted species or in tissue cultures, or by selection of temperature-sensitive variants. The first approach was that used by Edward Jenner who used a bovine poxvirus to vaccinate humans against smallpox.

Selecting attenuation through serial passages in a nontargeted species is the second approach that has been widely successful in obtaining live vaccines. For example, Parkman et al., *N. Engl. J. Med.*, 275: 569–574 (1966), developed an attenuated rubella vaccine after serial multiplication in green monkey kidney cells. A measle vaccine has been prepared by passaging the virus in chick embryo fibroblasts. Vaccines against, polio, hepatitis A, Japanese B encephalitis, dengue, and cytomegalovirus have all been prepared following similar procedures.

While animal models, and especially monkeys, are useful in developing live vaccines, a large uncertainty as to whether a vaccine is truly apathogenic remains until humans have been inoculated. For example, the Daker strain of yellow fever produced from infected suckling mouse brains induced encephalitis in 1% of vaccinees. Another crucial problem is the possible contamination of the vaccine, by exogenous viruses, during passages in cell culture or in animals, especially in monkeys. In light of the more recent knowledge of the potential danger of viruses that can be transmitted from animals to humans, this choice of developing live vaccines is highly questionable.

In contrast to the somewhat haphazard approaches of selecting for live vaccines, discussed above, modem developmental approaches introduce specific mutations into the genome of the pathogen which affects the ability of that pathogen to induce disease. Defined genetic manipulation is the current approach being taken in an attempt to develop live vaccines for various diseases caused by pathogenic microorganisms. Salmonella is a prime example of a pathogenic microorganism whose various species are the cause of a spectrum of clinical diseases that include acute gastroenteritis and enteric fevers. Salmonella infections are acquired by oral ingestion. The microorganisms after traversing the stomach, invade and replicate in the intestinal mucosal cells, Hornik et al., *N. Eng. J. Med.*, 283:686 (1970). Some species, such as, *S. typhi* can pass through this mucosal barrier and spread via the Peyer's patches to the lamina propria and regional lymph nodes. *Salmonella typhi* which only infects man is the cause of typhoid fever and continues to be an important public health problem for residents in the less developed world. The parenteral killed whole cell vaccine, now in use, is moderately effective but causes marked systemic and local adverse reactions at an unacceptably high frequency.

In an effort to develop live vaccines which are safer and elicit a higher immunological response researchers have focused their efforts to developing live vaccines having specific genetic mutations. Curtiss, in his U.S. Pat. No. 5,294,441, discloses that *S. typhi* can be attenuated by creating deletions ($\Delta$) in either or both the cya (adenylate cyclase) and crp (cyclic 3', 5'-AMP [cAMP] receptor protein) genes. cAMP and the cAMP receptor protein, the products of pleiotropic genes cya and crp, respectively, function in combination with one another to form a regulatory complex that affects transcription of a large number of genes and operons. Consequently, mutating either of these genes results in an attenuated microorganism. Furthermore, microorganisms having single mutations in either the cya or crp genes can not supplement their deficiency by scavenging these gene products from a host to be vaccinated. The crp gene product is not available in mammalian tissues and while the metabolite produced by the cya gene product, cAMP, is present in mammalian cells, the concentrations present in the cells which *S. typhi* invades are below the concentrations necessary to allow cya mutants to exhibit a wild-type phenotype. See, Curtiss et al., *Infect. Immun.*, 55:3035–3043 (1987).

Since cAMP is present in host tissues at some level, Curtiss et al., stabilized the $\Delta$cya microorganisms by introducing a mutation into the crp gene. Tacket et al., *Infect. Immun.*, 60(2):563–541 (1992), conducted a study with healthy adult inpatient volunteers which revealed that attenuated *S. typhi* having deletions in the cya and crp genes have the propensity to produce fever and bacteremia (bacteria in the blood).

A similar approach in the attempt to develop live vaccines has been taken by Dr. Stocker. The genes mutated by Stocker produce products which are also not available in host tissues. Stocker, in U.S. Pat. No. 5,210,035, describes the construction of vaccine strains from pathogenic microorganisms made non-virulent by the introduction of complete and non-reverting mutational blocks in the biosynthesis pathways, causing a requirement for metabolites not available in host tissues. Specifically, Stocker teaches that *S. typhi* may be attenuated by interrupting the pathway for biosynthesis of aromatic (aro) metabolites which renders Salmonella auxotrophic (i.e., nutritionally dependent) for p-aminobenzoic acid (PABA) and 2,3-dihydroxybenzoate, substances not available to bacteria in mammalian tissue. These aro-mutants are unable to synthesize chorismic acid (a precursor of the aromatic compounds PABA and 2,3-dihydroxybenzoate), and no other pathways in Salmonella exist that can overcome this deficiency. As a consequence of this auxotrophy, the aro-deleted bacteria are not capable of proliferation within the host; however, they reside and grow intracellularly long enough to stimulate protective immune responses. In the technical paper authored by Tacket et al., discussed above, attenuated strains of *S. typhi* were also constructed for use as vaccines by introducing deletions in the aro C and aro D genes, according to Stocker. These attenuated strains administered to healthy inpatient volunteers also have the propensity to produce fever and bacteremia.

Aside from the unacceptable side effects which result from the use of vaccine strains attenuated as a result of mutations in the cya and crp genes and the aro genes, the teachings of Curtiss and Stocker both suffer further limitations of only developing vaccines created by mutating a particular class of genes. That is, Curtiss and Stocker both teach that live vaccines may only be provided for by creating mutations in a class of genes whose products are not present in the host to be vaccinated at the concentrations necessary for the pathogen to proliferate. Consequently, there exists a vast potential for preventing additional diseases by providing live vaccines based on mutations which exist in a class of genes whose products are present in the host, to be vaccinated, at concentrations high enough for the pathogen to proliferate.

There is still a need, therefore, for vaccines that are prepared from live, non-virulent microorganisms, which are safe and when administered to a host will induce a highly effective type of immune response in the host susceptible to disease from corresponding pathogenic microorganisms.

SUMMARY OF THE INVENTION

Accordingly, it is an object of this invention to provide live vaccines for vaccinating a host against a pathogenic microorganism.

Another object of this invention is to provide a method whereby a vast array of vaccines, to prevent additional disease, may be produced by mutating genes that have not been previously capable of exploitation.

It is a further object of this invention to provide live vaccines which are attenuated as a result of introducing mutations into genes whose products are available in the vaccinated host.

It is yet another object of this invention to provide live vaccines which serve as carriers for immunogens of other pathogens, particularly microorganisms, including viruses, prokaryotes, and eukaryotes.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the method of this invention for preparing a live non-virulent vaccine from a virulent pathogenic microorganism comprises creating at least two mutations in a virulent strain of the pathogenic microorganism wherein the first mutation results in an auxotrophic mutant which requires for proliferation, a nutrient which is normally available in the host tissues in an amount required by the auxotrophic mutant for proliferation and the second mutation results in the inability of the auxotrophic mutant to specifically transport the required nutrient from the host tissues into the auxotrophic mutant.

BRIEF DESCRIPTION OF THE DRAWINGS

In the drawings.

The accompanying drawings, which are incorporated herein and form a part of the specification assist in illustrating the preferred embodiments of the present invention, and together with the description, serve to explain the principles of the invention. Furthermore, the accompanying drawings due to size limitations are not drawn to scale.

DETAILED DESCRIPTION OF THE PREFERRED EMBODIMENT

Vaccines prepared from live, non-virulent microorganisms are provided, according to this invention, for the immunization of a host which is susceptible to disease caused by the corresponding pathogenic microorganism. The live, non-virulent microorganisms may also serve as carriers for immunogens of other pathogens thereby producing a multiple immunogenic response. Pathogenic microorganisms, according to this invention, are made non-virulent as a result of non-reverting, non-leaky mutations that are created in at least two coding sequences, the products of which typically act in concert to produce and supply the microorganism with a nutrient that is required for the microorganism to proliferate. The first mutation blocks an enzyme pathway causing an absolute requirement for a nutrient which is normally available in the host, to be vaccinated, in amounts sufficient to allow proliferation of the microorganism, hence creating a nutritional mutant or auxotroph. The second mutation blocks the expression of a coding sequence which encodes a high-affinity transport protein which is required to specifically transport the nutrient, required by the auxotroph for proliferation, from the outside environment into the microorganism. The vaccine strains are viable and may be grown and maintained on media supplemented with excessive concentrations of the required nutrient; as the required nutrient will be scavenged by the microorganism either passively or by some low-affinity transport protein, thus complementing the auxotrophy. However, the vaccine strains when introduced into a host will continue to live (until eliminated by the host's immune system) but will be unable to proliferate as a consequence of the non-reverting, non-leaky mutations.

Essentially the live vaccines provided for, according to the present invention, originate with an auxotrophic pathogenic microorganism. A non-reverting mutation is introduced into a gene, of a pathogen, encoding a functional enzyme which is indispensably required for a particular step in a biosynthetic pathway, thus, resulting in an auxotrophic pathogen. Since the product of the disabled pathway is available in the host to be vaccinated, it becomes necessary to create a second non-reverting mutation, or set of non-reverting mutations in the auxotrophic pathogen, which disables the pathogen's ability to specifically scavenge the required product from the vaccinated host; otherwise, the auxotrophic pathogen will supplement its auxotrophy by specifically scavenging the required product present in the host, proliferate and cause the occurrence of disease. Thus, although the needed nutrient is present in the host at the concentrations necessary for the proliferation of the auxotrophic pathogen, the mutated pathogen as a result of the second mutation or set of mutations is unable to proliferate, even though it is alive and retains its native antigenic characteristics.

In general, microorganisms have the ability to constantly monitor and regulate, through positive and negative regulatory mechanisms, the intracellular concentrations of various compounds, such as amino acids and other nutrients. When a microorganism senses that there is a deficiency for a particular product, counteractive measures are initiated in order to supplement the deficiency. The first measure taken by the microorganism may be to increase the expression of the gene responsible for producing the deficient product. In the event the gene responsible for producing the deficient product has been disabled, the microorganism relies on its ability to transport the required compound, for which it is deficient, from the outside environment across the cell membrane and into the microorganism where the compound can be utilized for its intended purpose.

There exists a vast array of transport systems, the regulation of which have varying degrees of complexity. However, all transport systems whether simple or complex, ultimately rely upon the expression of specific periplasmic or transporter proteins having high binding affinities which function to transport specific compounds across the cell membrane. Consequently, expression of a transporter system can be disrupted by specifically disabling the coding sequence(s) that is responsible for the expression of any component involved in transport or in the alternative, it is possible to disrupt the coding sequence(s) whose product(s), are responsible for activating or regulating the expression of the coding sequence that encodes the components of the transporter system.

The choice of genes to be disabled will be governed by the ability to mutate the genes without destroying the viability of the microorganism; and by the presence of a high-affinity transport system which complements the microorganism's deficiency. The disabled genes must prevent production of an enzyme required in the biosynthetic pathway of a nutrient necessary for proliferation and must prevent the transport of the required nutrient from the outside environment without effecting the in vitro viability of the microorganism. Genes of particular interest include several genes under nitrogen control, such as genes involved in the production and transport of histidine, glutamine, lysine-arginine-ornithine, and glutamate-aspartate. However, there are many other examples of biosynthetic pathways and complementary transport systems, of other amino acids and nutrients that are well defined both genetically and biochemically that enable an auxotrophic microorganism to overcome short term, long term, or permanent deficiencies of required compounds, which could be exploited by the teachings of the present invention.

The following discussion is intended to be illustrative of the present invention and is not intended to limit the scope of the present invention to the following specific example, as it is contemplated that live, non-virulent vaccines may be prepared by disabling the respective transport systems of all auxotrophic pathogens that are capable of supplementing their deficiency upon introduction into a host to be vaccinated.

To illustrate the workings of the present invention the biosynthetic pathway and transport system of the amino acid glutamine has been chosen, as these complementary systems exemplify the class of genes from which live vaccines may be provided for, according to the present invention. In addition, glutamine is present in the tissues of a vertebrate host, to be vaccinated, at concentrations clearly high enough to sustain growth of a glutamine auxotroph. See, experimental evidence presented below, and Bloom, "Tuberculosis: Pathogenesis, Protection and Control," *American Society for Microbiology*: 353–385 (1994).

The synthesis of a number of bacterial proteins is controlled by the availability of combined nitrogen in the growth medium, and in most instances is increased under nitrogen-limiting conditions. These proteins provide the bacterial cell with glutamate and glutamine which, in turn, provide most of the cellular nitrogen present for the synthesis of macromolecules in the bacteria. The only other source of cellular nitrogen is derived directly from the incorporation of ammonia. Glutamate provides nitrogen, derived from the amino group, for the synthesis of most of the amino acids; whereas, glutamine provides nitrogen, derived from the amido group, for the synthesis of purines, pyrimidines, amino sugars, histidine, tryptophan, asparagine, NAD, and p-aminobenzoate. Glutamine is the end product of a reaction responsible for ammonia assimilation and catalyzed by the enzyme glutamine synthetase. Mutations in glnA, the structural gene for glutamine synthetase, result in an absolute requirement for glutamine; thus glnA is the only gene encoding for glutamine synthetase. Therefore, glutamine synthetase has two functions: the assimilation of ammonia when the growth of the cell is limited by the availability of ammonia and the synthesis of glutamine.

Below, is a brief overview of the regulation of the transcriptional regulation of glutamine synthetase and glutamine transport in *Salmonella typhimurium* and *Escherichia coli*. In general, transcription involves three distinct stages of reaction: initiation, elongation and termination. The first and last encompass the interactions by which an enzyme, RNA polymerase, binds to DNA to start RNA synthesis or disassociates from it at the cessation of synthesis. Between these stages, the central process of RNA synthesis involves the movement of RNA polymerase along DNA, producing an RNA chain whose sequence is determined by the DNA template. Initiation involves the formation of a complex between RNA polymerase and DNA at the site that surrounds the first base to be transcribed into the RNA. The entire sequence of DNA that is necessary for complex formation is called the promoter. The point at which the first nucleotide is incorporated is called the startsite or startpoint.

Figure 2:
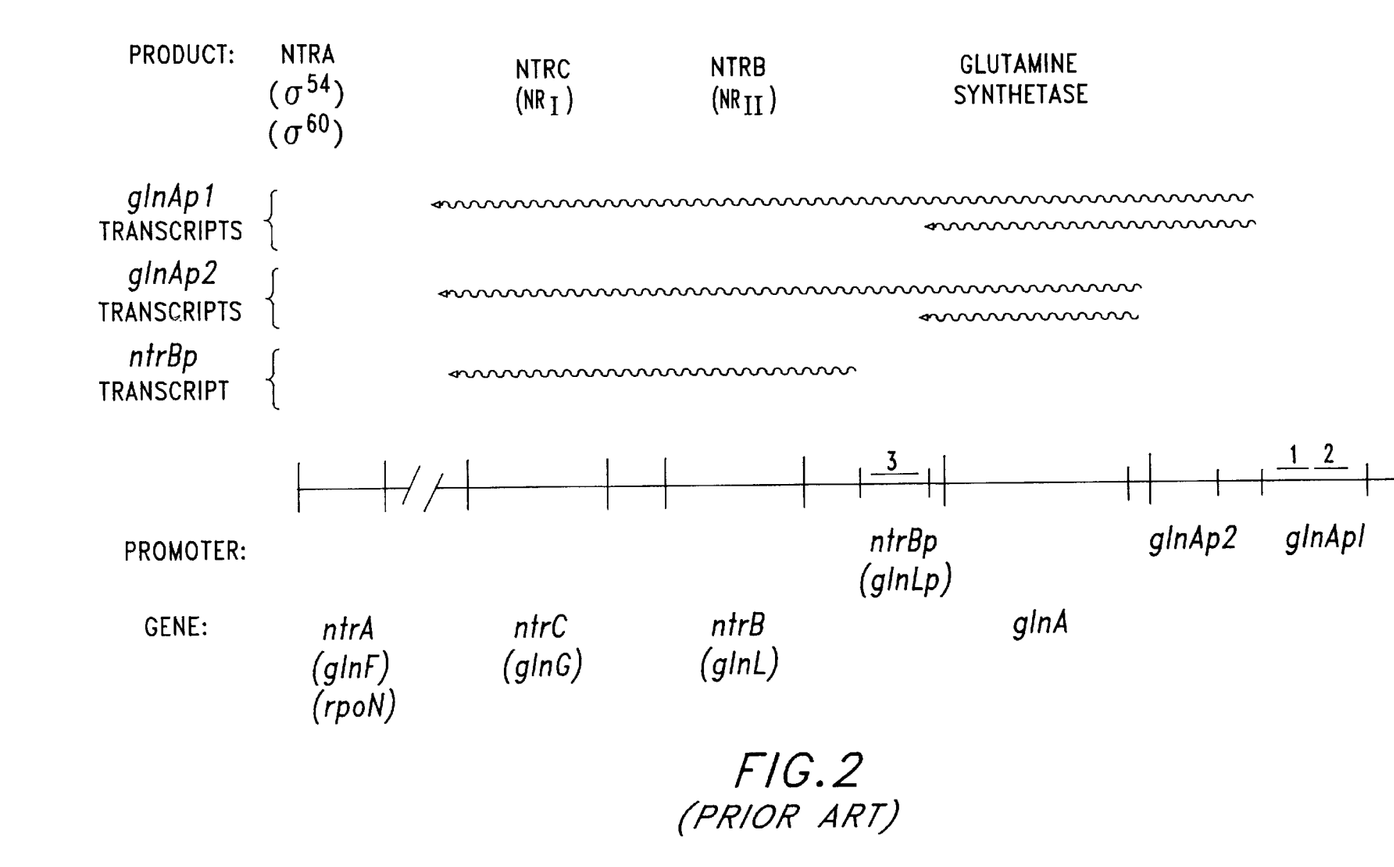
FIG. 2 is a schematic representation of the glnA ntrBC operon.

Glutamine synthetase levels are modulated by controlling the level of transcription of glnA. glnA is a member of the glnA ntrBC operon, shown in FIG. 2, which includes in addition to glnA, two other nitrogen regulatory genes ntrB and ntrC, also referred to as glnL and glnG, respectively. Three promoters exist in the glnA ntrBC operon. glnAp1, with a transcriptional startsite located 187 base pairs (bp) upstream from the translational startsite in glnA; glnAp2, with a transcriptional startsite 85 bp upstream from the translational startsite in glnA; and ntrBp, with a transcriptional site located 256 bp downstream from the translational termination site in glnA and 33 bp upstream from the translational startsite in ntrB. Reitzer and Magasanik, *Escherichia coli* and *Salmonella typhimurium,* Cellular and Molecular Biology, American Society of Microbiology, pp. 302–320 (1987), herein incorporated by reference.

Under conditions of nitrogen excess, both NTRC and NTRB (also referred to as $NR_I$ and $NR_{II}$, respectively) the nitrogen regulatory proteins of structural genes ntrC and ntrB, respectively, exist at low levels predominantly in their inactive forms. NTRC is a DNA binding protein that recognizes and binds two adjacent sequences (labeled 1 and 2, in FIG. 2) located within the glnAp1 promoter and one sequence (labeled 3) located within ntrBp. Transcription of glutamine synthetase, under nitrogen excess conditions, occurs at low levels through activation of glnAp1 by $\sigma^{70}$ RNA polymerase.

RNA polymerase or the holoenzyme, as it is commonly referred to, can be separated biochemically into two components, the core enzyme and the sigma factor (the σ polypeptide). The names reflect the fact that only the holoenzyme can initiate transcription; but then the sigma "factor" is released, leaving the core enzyme to undertake elongation. The function of the sigma factor is to ensure that RNA polymerase binds stably to DNA and initiates transcription only at promoters, not at other sites. Sigma factor also confers the ability to recognize specific binding sites and different sigma factors recognize different promoters. Therefore, $\sigma^{70}$ is the sigma factor, discussed previously, responsible for recognizing the glnAp1 promoter and initiating transcription of glutamine synthetase.

When nitrogen becomes limiting, NTRB is activated in response to a lower level of internal glutamine such that it causes phosphorylation of NTRC; NTRC-phosphate then acts as a transcriptional activator, activating initiation of transcription at glnAp2 by $\sigma^{54}$-RNA polymerase ($\sigma^{54}$ associated with core RNA polymerase). NTRC phosphate catalyzes the isomerization of the closed $\sigma^{54}$-RNA polymerase promoter complex to an open complex. Consequently, glutamine synthetase expression is initiated at the major glnA promoter, glnAp2, resulting in high levels of glutamine synthetase, NTRB and NTRC in order to increase internal glutamine levels. The resulting increase in the level of NTRC furthermore results in the complete repression of transcription initiating at glnAp1 and ntrBp. As discussed previously, NTRC binding sites exist within glnAp1 and ntrBp and as a result of the increasing levels of NTRC-phosphate bound at these sites $\sigma^{70}$ RNA polymerase is prevented from recognizing and initiating transcription at the glnAp1 and ntrBp promoters. Shifting the microorganisms from nitrogen starvation to nitrogen excess causes NTRB to facilitate the removal of phosphate from NTRC-phosphate, bringing an end to the initiation of transcription at glnAp2. Continued growth in this nitrogen rich media results in the decline of levels of glutamine synthetase and NTRC by dilution. Consequently, the repression of glnAp1 and ntrBp by NTRC is lifted sufficiently to allow both glutamine synthetase and NTRC to be maintained at their respective low levels.

$\sigma^{54}$ (also referred to as $\sigma^{60}$, $\sigma^{N}$, or NTRA) is encoded by the structural gene ntrA (alternately designated glnF or rpoN) and, as discussed above, is a positive regulatory factor needed for the expression of the gene encoding glutamine synthetase from the major glnAp2 promoters. $\sigma^{54}$, is required for the transcription of the nitrogen fixation (nif) genes in a number of bacteria, and is required for transcription of genes encoding amino acid transport, such as glutamine, degradative enzymes, as well as many other genes. See, Dixon, R., *J. Gen. Microbiol.*, 130:2745–2755 (1984), Magasanik, B., *Annu. Rev. Genet.*, 16:135–168 (1982), and S. Kustu et al., *Micro. Biol. Reviews*, 53:367–376 (1989).

Figure 3:
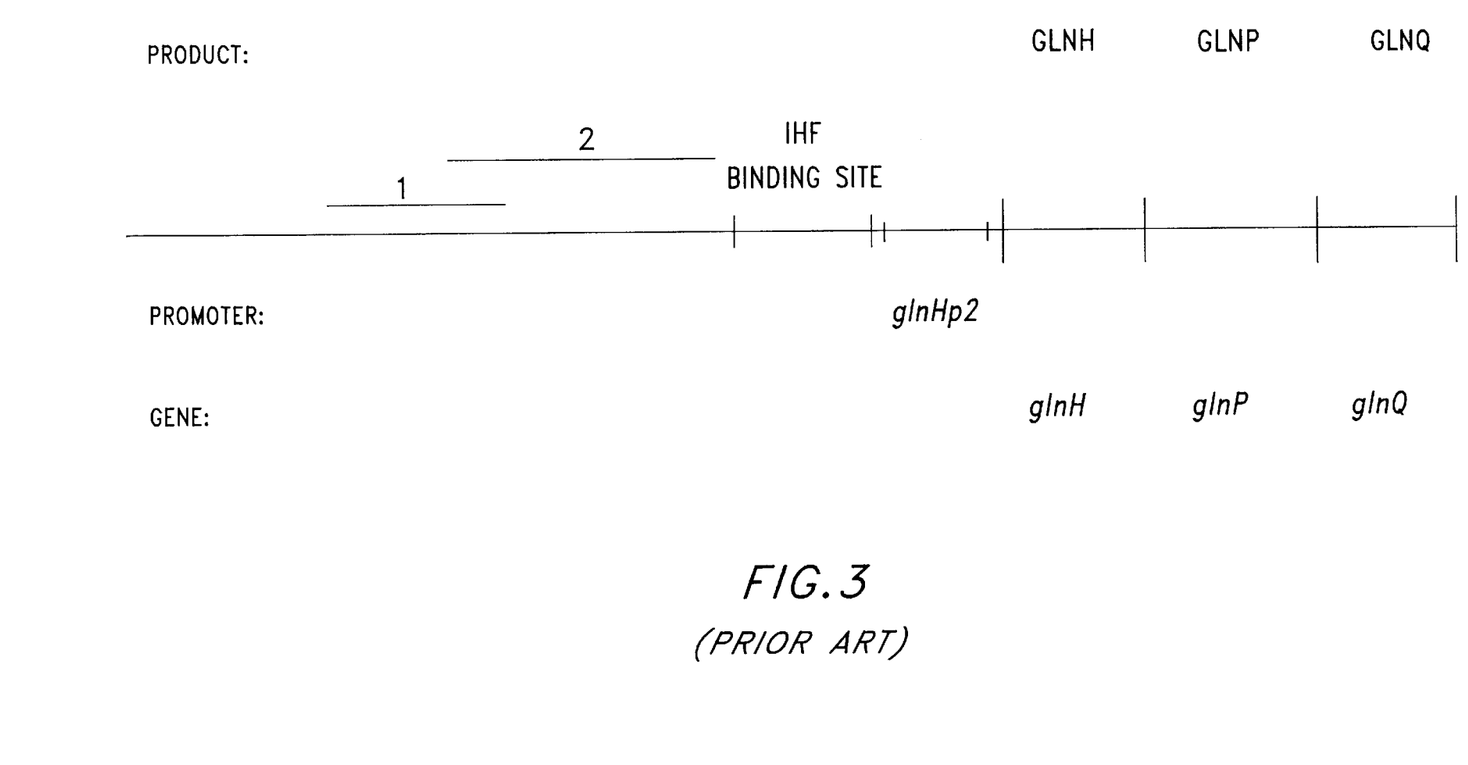
FIG. 3 is a schematic representation of the glnHPQ operon.

The glnHPQ operon, shown in FIG. 3, encodes the components of the high-affinity glutamine transport system and its expression is induced under nitrogen limiting conditions. Under nitrogen limiting conditions NTRC-phosphate, discussed previously, binds to two overlapping sites (labelled 1 and 2) located upstream from the glnHp2 promoter, and activates transcription of glnHp2 by catalyzing isomerization of the closed $\sigma^{54}$-RNA polymerase promoter complex to an open complex. The DNA-binding protein, integration host factor (IHF), binds to a site immediately upstream of glnHp2 and enhances the activation of open complex formation by NTRC-phosphate. Mutations in glnH, the structural gene for the high-affinity periplasmic glutamine binding protein (GLNH) results in microorganisms having a marked decrease in the ability to transport glutamine due to a loss of the glutamine binding protein or loss of its binding activity. Kustu et al., *J. Bacteriol.*, 138(1): 218–234 (1979). Kustu et al., however, observed a second component of glutamine transport, wherein cells with reduced uptake of glutamine via the high-affinity glutamine transport system are capable of transporting small amounts of glutamine, if the available glutamine is present in excessive quantities.

Consequently, a mutation that permanently disables a microorganisms ability to produce a necessary nutrient, also demands activation of the microorganism's transport system for that specific nutrient which the microorganism is deficient for. Disabling the same microorganism's specific transport system results in a microorganism that is viable in conditions where the required nutrient is present in excessive concentrations; however, the microorganism when introduced into an environment, such as a vertebrate, where the required nutrient is present at normal levels (i.e., at levels necessary for an auxotrophic microorganism to proliferate) will continue to live, until eliminated by the host's immune system, but are surprisingly unable to proliferate and cause disease.

There are a number of well known techniques which can be employed for disabling or mutating genes, such as the employment of translocatable elements, mutagenic agents, transducing phages, and DNA-mediated transformation, and/or conjugation. Other methods also known to one with ordinary skill in the art such as recombinant DNA technology may also be employed to successively introduce one or more mutated genes into a single host strain to be used as the vaccine.

In accordance with the subject invention, vaccines are produced by introducing a non-reverting mutation into at least two genes, where each mutation is large enough to insure a substantially zero probability of reversion and assurance of the non-expression of each mutated gene. In addition, each gene chosen will be involved in either the production of or the transport of the same nutrient. The type of genes chosen to produce the vaccine will result from the likelihood that the first gene to be mutated must prevent the production of an enzyme required in the biosynthetic pathway of a nutrient that is present in the host to be vaccinated in quantities sufficient for proliferation, and the second gene(s) to be mutated will express components of a corresponding high-affinity transport system required for the transport of the required nutrient. These requirements have been shown to be fulfilled by the genes involved in the synthesis and transport of glutamine, so that these genes are preferred, although other genes, as previously indicated, may also serve as the site for the non-reverting mutations. In the case of glutamine it is essential to first create a glutamine auxotroph by permanently mutating the glnA gene. A second non-reverting mutation is then introduced into either glnH or glnQ, the genes responsible for the expression of the transport proteins that bind and transport glutamine from the outside environment, across the microorganism's cell membrane and into the microorganism. The construction of such strains and their efficacy is described in detail in the Examples section which follows.

In the second embodiment of the present invention the vaccines are produced by introducing non-reverting mutations in at least two genes, where each mutation is large enough to insure a substantially zero probability of reversion and assurance of the non-expression of each mutated gene. The first gene chosen will be involved in the production of an enzyme required in the biosynthetic pathway of a particular nutrient that is present in the host, to be vaccinated, in quantities sufficient for proliferation. The second gene or genes chosen will be involved in regulating the expression of the corresponding high-affinity transport system for the required nutrient. In the case of glutamine, a glutamine auxotroph is first created by permanently mutating the glnA gene. A second non-reverting mutation or set of mutations is created in either ntrA, ntrC, or both ntrA and ntrC, the genes that are involved in the regulation of the glutamine transport operon, glnHPQ. The construction of such strains and their efficacy is described in detail in the Examples section which follows.

In a third embodiment live vaccines prepared in accordance with the present invention may be used as vectors or carriers for antigens of species other than the non-virulent pathogenic vaccine. One or more structural genes coding for the desired antigens may be introduced into the non-virulent pathogenic vaccine as an expression cassettes. The expression cassette comprises the structural gene or genes of interest under the regulatory control of the transcriptional and translational initiation and termination regions which naturally border the structural gene of interest. Where bacterial or bacteriophage structural genes are involved, the natural or wild-type regulatory regions will usually, but not always, suffice. It may be necessary to join regulatory regions recognized by the non-virulent pathogen to structural genes for antigens isolated from eukaryotes and occasionally prokaryotes.

The expression cassette may be a construct or may be or form part of a naturally occurring plasmid. If the expression cassette is a construct, it may be joined to a replication system for episomal maintenance or it may be introduced into the non-virulent pathogenic microorganism under conditions for recombination and integration into the non-virulent pathogen's chromosomal DNA. Structural genes for antigens of interest may encode bacterial proteins such as toxin subunits, viral proteins such as capsids, or enyzme pathways such as those involved in synthesis of carbohydrate antigens such as lipopolysaccharide (LPS). For example among the antigens expressed in other live attenuated Salmonella vaccines are Fragment C of tetanus toxin, the B subunit of cholera toxin, the hepatitis B surface antigen, and *Vibrio cholerae* LPS. Additionally, the HIV antigens GP120 and GAG have been expressed in attenuated *Mycobacterium bovis* BCG and *Shigella soneii* LPS has been expressed in attenuated *Vibrio cholerae*. The construct or vector may be introduced into the host strain through a number of well known methods, such as, transduction, conjugation, transformation, electroporation, transfection, etc.

In an alternate embodiment, live vaccines prepared in accordance with the preferred embodiment which have non-reverting mutations in genes under nitrogen control may be used as vectors or carriers for antigens of species other than the non-virulent pathogenic vaccine. One or more structural genes coding for the desired antigens may be operatively linked to an ntr-regulated promoter. As the non-virulent pathogenic microbe senses a nitrogen deficiency, expression of the ntr genes increases accordingly, thus initiating expression of genes transcribed from ntr promoters. For example, one or more structural genes coding for the desired antigens may be operatively linked to the glnAp2 promoter located on a suicide vector or an autonomously replicating plasmid. The suicide vector or plasmid may then be introduced into the non-virulent pathogenic strain having non-reverting mutations located in the genes glnA and glnH or glnQ, by well known methods, such as, transduction, transformation, electroporation, tri-parental mating techniques or direct transfer of a self mobilized vector in a bi-parental mating and maintained within the microorganism either autonomously or in the bacterial host's chromosomal DNA. Therefore, under low internal glutamine conditions which this attenuated strain must experience, the glnAp2 promoter will be activated and express the structural genes that have been operatively linked thereto. As discussed, in detail above, activation of an ntr promoter requires the proteins NTRA and NTRC, therefore this alternate embodiment will only work if the ntrA and ntrC genes are fully functional. Thus, this particular embodiment would be based on a strain prepared according to the preferred embodiment of the present invention and not the second embodiment of the present invention.

The following non-limited examples provide vaccines prepared from live, non-virulent microorganisms, according to the teachings of the present invention. All scientific technical terms have the meanings as understood by one with ordinary skill in the art. Recombinant DNA techniques are now sufficiently well known and widespread so as to be considered routine. In very broad and general terms, this method comprises transferring the genetic material of one organism into a second organism so that the transferred genetic material becomes a part of the genetic material of the organisms to which it is transferred. This typically consists of first obtaining a piece of DNA from the first organism either from a plasmid or the chromosomal DNA. The piece of DNA may be of any size and is often obtained through the use of restriction endonuclease enzymes which recognize and cut DNA at specific base pair sites. Following the isolation of a particular piece of DNA, the DNA may be inserted or cloned into plasmid, phage or cosmid vectors to form recombinant molecules that may be subsequently transferred into a host cell by various means such as transformation, transduction, transfection, conjugation, etc.

Transformation involves the uptake of naked DNA from the external environment, which can be artificially induced by the presence of various chemical agents, such as calcium ions or by electroporation. Transduction involves the packing of the recombinant DNA within a phage, such as transducing phage or cosmid vectors. Once the recombinant DNA is introduced into the microbial host, it may continue to exist as a separate piece or it may insert or integrate into the host cell's chromosome and be reproduced with the chromosome during cell division. Conjugation involves classical microbial mating techniques.

All restriction enzymes and pBR322 can be purchased from Stratagene, 11099 North Torrey Pines Rd., La Jolla, Calif. 92037. Electroporation was carried out with a BioRad Gene Pulser apparatus Model No. 1652098. *S. typhimurium* cells were prepared as per the manufacturer's instructions. Aliquots of competent cells were mixed with an aliquot of the desired plasmid and placed on ice for 1 minute. The mixture was transferred into a cuvette-electrode (1.9 cm) and pulsed once at a field strength of 12.5 KV/cm as per the manufacturer's instructions.

The above disclosure generally describes the present invention. A more complete understanding can be obtained by reference to the following specific examples which are provided herein for purposes of illustration only and are not intended to be limiting unless otherwise specified.

Construction of Microbial Auxotroph

Figure 4:
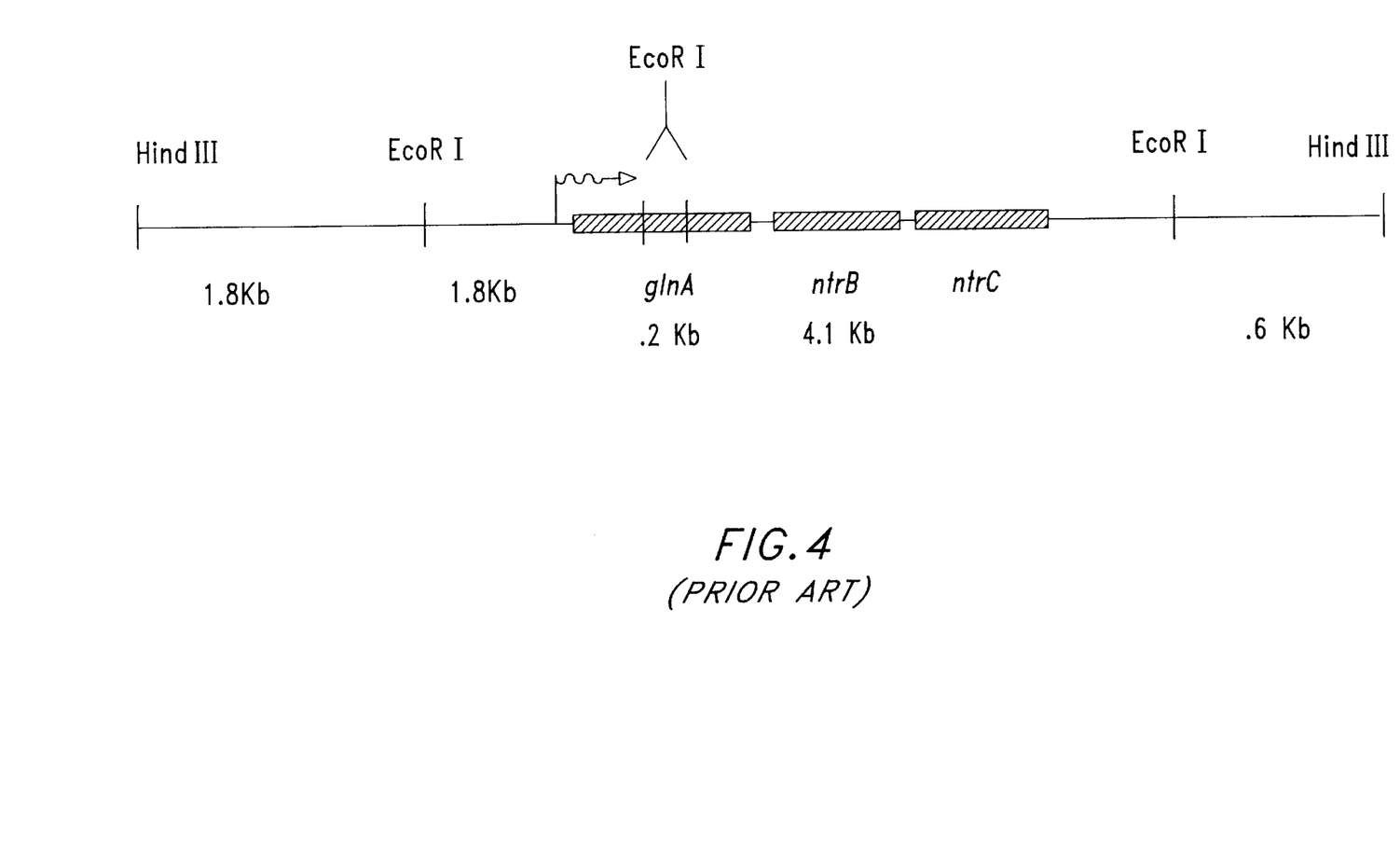
FIG. 4 is a schematic representation of a DNA fragment from *Salmonella typhimurium* which contains the glnA ntrBC operon used to construct a strain having a non-polar deletion in the glnA gene.

The 8.9 Kb Hind III *S. tphimurium* chromosomal fragment, shown in FIG. 4, (Koduri et al., *Gene,* 11:227–237

(1980), incorporated herein by reference, contains the entire glnA operon and is inserted into pBR322 digested with Hind III, to form pJES89. A large scale isolation of plasmid DNA, pJES89, was performed according to T. Maniatis et al., Molecular Cloning: A Laboratory Manual, Cold Spring Harbor Laboratory Press, Cold Spring Harbor, N.Y., 1989, and the isolated plasmid DNA was digested with EcoRI, followed by gel electrophoresis to separate the various fragments. The two fragments of interest are 1.8 Kb and 4.1 Kb in length. The 1.8 Kb EcoRI fragment contains the glnA promoter region and the coding sequence for the N-terminus of glutamine synthetase (glnA') and was subsequently subcloned into pBR322 digested with EcoRI to form pJES31. The 4.1 Kb EcoRI fragment contains the coding sequence for the C-terminus of glutamine synthetase ('glnA) and the entire coding sequences of ntrB and ntrC, and was subsequently subcloned into pBR322 digested with EcoRI to form pJES41.

Large scale isolations of plasmids pJES31 and pJES41 were performed, as discussed in Maniatis et al., Id. The 1.8 Kb EcoRI fragment was isolated and purified from pJES31 and cloned into pMAK705 (Hamilton et al., J. Bact., 171:4617–4622 (1989) which was partially digested with EcoRI, resulting in pKEK3. pMAK705 is a temperature sensitive suicide vector; at 30° pMAK705 can replicate autonomously, however, at 40° C. pMAK705 is unable to replicate. Selecting for chloramphenicol resistance at 40° C. requires cointegrate formation. The 4.1 Kb EcoRI fragment was next isolated and purified from pJES41 and inserted into pKEK3 which was partially digested with EcoRI, resulting in pKEK4. pKEK4 contains the 1.8 Kb and the 4.1 Kb EcoRI fragments in the correct orientation to produce a non-functional glutamine synthetase enzyme which lacks amino acids 41–130, corresponding to the deleted 200 base pair EcoRI fragment of glnA, shown in FIG. 4.

pKEK4 was then electroporated into competent S. typhimurium cells from ATCC strain 14028, as described above, and incubated at 30° C. in LB (Luria broth)+2 mM glutamine (gln) for one hour, then plated on LB+Cm$^{20}$ (20 μg per ml of chloramphenicol)+gln$^{2\ mM}$ at 40° C. overnight. The resulting colonies were streaked out for single colonies on LB, Cm$^{20}$, gln$^{2\ mM}$ at 40° C. overnight. A single colony (cointegrant) was inoculated into LB+gln$^{2\ mM}$ at 30° C. and allowed to reach saturation. This culture was diluted 1:1000 into LB+gln$^{2\ mM}$ and allowed to reach saturation at 30° C. Finally, this saturated culture was diluted in 1×PBS and plated on LB+gln$^{2\ mM}$ at 30° C. such that the plates would contain approximately 100 colonies; 50 colonies were scored for Gln$^-$ and Cm$^s$ phenotypes. A colony having the Gln$^-$ Cm$^s$ phenotype was isolated and is referred to as KK27 (ΔglnA1).

Construction of Strains Having Mutations in the Nitrogen Regulatory Genes

Media:

Luria broth, in liquid and on agar plates, was routinely supplemented with 2 mM glutamine to allow growth of strains with reduced levels of glutamine synthetase, and supplemented with antibiotics when appropriate. Nutrient broth and minimal glucose media with ammonia as sole nitrogen sources were used as indicators of glutamine auxotrophy. Green indicator plates (1 L total volume: 10 g Tryptone, 5 g Yeast Extract, 5 g NaCl, 2.5 g Glucose, 15 g Agar, 20 ml of 12.5% $K_2HPO_4$, 1.25 ml Evans Blue and 2.5 ml 1% Sodium Fluorescein) supplemented with 2 mM glutamine were utilized to phage-purify all strains constructed. See, Cold Spring Harbor Laboratories, Advanced Bacterial Genetics Laboratory Manual, In Press.

Strain Construction:

All Salmonella typhimurium strains used are isogenic with American Tissue Culture Collection (ATCC) strain 14028, a smooth virulent strain of S. typhimurium referred to as "wild-type". Tn10 insertions in nitrogen regulatory genes, ntrA, ntrB or ntrC were introduced into wild-type strains by P22HTint.-mediated transduction from donor strains SK284 (ntrA209::Tn10), SK398 (ntrB137::Tn10), SK835 (ntrC352::Tn10) and SK811 (zig 214::Tn10, a transposon linked to ntrC) to form strains KK1 (ntrA209::Tn10), KK10 (ntrB137::Tn10), KK2 (ntrC352::Tn10) and KK14 (zig214::Tn10), respectively. All strains designated SK were received from Dr. Sydney Kustu, Department of Molecular and Cellular Biology, University of California, Berkeley, Calif. 94720. See, Kustu et al., Mol. Gen. Genet., 192:187–197 (1983), incorporated herein by reference. Bacteriophage P22HTint. lysate from SK811 (zig214::Tn10) was used to transduce strain SK35 [Δ(glnA-ntrC)60], Kustu et al., Id., to tetracycline resistance while retaining glutamine auxotrophy, thus linking the deletion to a transposon marker; the resulting strain was used as a donor to transduce ATCC strain 14028 to tetracycline resistance and glutamine auxotrophy forming strain KK4 [Δ(glnA-ntrC)60; zig214::Tn10].

Construction of Strains Having Mutations in the High-Affinity Transport Genes

Strain Construction:

Degenerate oligonucleotide primers were synthesized using an oligonucleotide synthesizer, Expedite Model 8909; Millipore, Inc., as per the manufacturer's instructions based upon the published amino acid sequence of the E. coli glnH and glnQ genes (T. Nohno, et al., Mol. Gen. Genet., 205:260–269 (1986)). The primers of the glnH fragment used for the polymerase chain reaction (PCR; Perkin-Elmer Cetus) or amplification were GLNH1: 5'-GC GGATCCTTYGTNCCNTTYGARTTYAA-3' (SEQ ID NO. 1) and GLNH2: GCG GAATTCARYTCCATRTANGCRTTRTC-3' (SEQ ID NO. 2), the underlined nucleotides represent restriction sites for BamHI and EcoRI, respectively, N=any nucleotide, Y=pyrimide, and R=purine. Only one fragment, approximately 400 base pairs in length, was produced from ATCC strain 14028 chromosomal DNA, which corresponds to the sense strand from base pairs 35 to 168 of the published glnH sequence (based on comparison with E. coli gene; partial sequencing of this fragment confirmed homology to Escherichia coli glnH). PCR was carried out in a buffer containing 2.0 mM Mg$^{2+}$ for 30 cycles of 45 seconds at 92° C., 1 minute at 42° C. and 1 minute 30 seconds at 72° C. This procedure was carried out in a DNA Thermal Cycler #N801-0150 (Perkin-Elmer Cetus). The amplified fragments were then digested with EcoRI and BamHI and ligated into pBR322 cut with EcoRI and BamHI, to form pKEK11.

Primers for the amplification of the glnQ fragment were GLNQ1: 5'-GCGGAATTCCG GNATGGTNTTYCARCARTT-3' (SEQ ID NO. 3) and GLNQ3: 5'-GGCGAAGCTTACYT GNGGRTTNCCRTCYTC-3' (SEQ ID NO. 4), the underlined nucleotides represent restriction sites for EcoRI and Hind III, respectively, N=any nucleotide, Y=pyrimide, and R=purine. One fragment, approximately 430 base pairs in length, was produced from ATCC strain 14028 chromosomal DNA, which corresponds to the sense strand from base pairs 80 to 222 of the published glnQ sequence (based on comparison with E. coli gene; partial sequencing of this fragment confirmed homogy to Escherichia coli glnQ). PCR was carried out as described above and the amplified fragments were digested with EcoRI and Hind III and ligated into pBR322 cut with EcoRI and Hind III to form pKEK12.

pKEK11 and pKEK12 were then separately digested with BamHI and HindIII, respectively. The ends of the resulting restriction fragments were then filled-in with Klenow (New England Biolabs), (T. Maniatis, Molecular Cloning: A Laboratory Manual, Cold Spring Harbor Laboratory Press, Cold Spring Harbor, New York, 1989). The resulting fragments were digested with EcoRI and ligated into a suicide vector pGP704, previously digested with EcoRV and EcoRI, to form pKEK13 and pKEK14, respectively. pGP704 is a broad host range suicide vector that comprises the β-lactamase or bla gene which confers ampicillin resistance, a mobilization fragment or mob which contains the origin of transfer (ori T), thus, allowing for mobilization of pGP704, the origin of replication from plasmid R6K or oriR6K, and multiple cloning site or polylinker. The R6K origin of replication (oriR6K) requires for its function a protein called Pi, which is encoded for by the pir gene, which is supplied in trans by an E. coli strain SM10λpir. V. Miller et al., J. Bacteriol., 170:2575 (1988), available from Dr. J. Mekalanos Department of Microbiology and Molecular Genetics, Harvard Medical School, 200 Longwood Avenue, Boston, Mass. 02115 and Dr. V. DiRita Department of Microbiology and Immunology, University of Michigan Medical School, Ann Arbor, Mich.

Plasmids pKEK13 and pKEK14 were electroporated, under conditions discussed previously, into competent λpir S. typhimurium cells, strain SL4213F' λpir, to obtain protective methylation, and the plasmids were then isolated and purified. Mahan et al., J. Bact., 175:7086–7091 (1993). Strain SL4213F' λpir is available from Dr. J. Mekalanos, Department of Microbiology and Molecular Genetics, Harvard Medical School, 200 Longwood Avenue, Boston, Mass. 02115, and Dr. Michael Mahan, University of California at Santa Barbara, Department of Biological Sciences, Santa Barbara, Calif. 93106. However, any S. typhimurium expressing the pir gene will suffice.

SL4213F' λpir cells were prepared for electroporation as per the manufacturer's instructions. Two aliquots of cells were mixed with an aliquot of pKEK13 and an aliquot of pKEK14, respectively, and placed on ice for 1 minute. The mixture was transferred into a cuvette-electrode (1.9 cm) and pulsed once at a field strength of 12.5 kV/cm, as per the manufacturer's instructions. The mixture was then added to 1 ml SOC medium (2% tryptone, 0.5% yeast extract, 10 mM, NaCl, 25 mM KCL, 10 mM MgCl$_2$, 10 mM MgSO$_4$, 20 mM glucose) and shaken at 37° C. for 1 hour and plated on LB gln$^{2mM}$ Amp$^{100\mu g/ml}$. Plasmids pKEK13 and pKEK14 were then isolated and purified as per Maniatis, Id.

Purified plasmids pKEK13 and pKEK14, having protective methylation, were then electroporated into competent S. typhimurium cells, strain ATCC 14028, which do not contain λpir, and grown in SOC for one hour at 37°. The cells were then plated out on LB gln$^{2mM}$ Amp$^{100\mu g/ml}$. Colonies that appear were presumed to be ampicillin resistant (amp$^r$) due to the cointegration of pKEK13 or pKEK14 into the chromosomal DNA within the glnH (pKEK13) or glnQ (pKEK14) genes, respectively. Homologous recombination of plasmids pKEK13 and pKEK14 with the respective glnH and glnQ genes is demanded for; otherwise the suicide vector due to its inability to replicate is lost and all resulting progeny of strain 14028 will be ampicillin sensitive and thus selected against.

The insertion caused by the cointegration of pKEK13 into the chromosomal DNA of strain 14028 [glnH1::pGP704 (Amp$^R$)] was moved by P22-mediated transduction into ATCC 14028 to form strain KK44 (glnH1::pGP704). The insertion caused by the cointegration of pKEK14 into the chromosomal DNA of strain 14028 [glnQ1::pGP704 (Amp$^R$)] was moved by P22-mediated transduction into ATCC 14028 to form strain KK49 (glnH1::pGP704). All transductants were purified free from phage on green plates supplemented with 2 mM glutamine.

Media:

Minimal media Bancroft, et al., J. Bact., 134:1046–1055, (1978) agar plates supplemented with 0.4% glucose as carbon source and 10 mM glutamate as nitrogen source were overlaid with 100 μl of 100 mM γ-glutamyl hydrazide and mutant growth phenotype was assessed at 37° C. after 24 and 48 hours; glnHPQ mutants are able to grow in the presence of the toxic glutamine analog, whereas strains with an intact glutamine permease operon are killed or grow much slower Kustu, et al., J. Bact., 138:218–234,(1979), T. Nohno, et al., Mol. Gen. Genet., 205:260 (1986).

S. typhimurium strains SK359 (glnH141; ntrB128; hisF645) and SK364 (glnH146; ntrB128; hisF645) were used as reference strains, comparing their growth against their parental isogenic strain SK214 (ntrB128; hisF645—in these instances, the plates were additionally overlaid with 100 μl 100 mM L-histidine, as these strains are also histidine auxotrophs). Strains KK44 and KK49 displayed glnHPQ phenotypes on this medium, compared to their parental isogenic strain ATCC 14028.

EXAMPLES

Example 1

This example describes the construction of a non-virulent or avirulent microbial strain, according to the preferred embodiment of the present invention, having at least two mutations, wherein the first mutation creates an auxotroph by blocking a gene that encodes a functional enzyme that is indispensably needed for a particular step in a biosynthetic pathway which produces a necessary nutrient, and the second mutation blocks a gene that encodes a protein belonging to a high-affinity transport system which is required to complement the auxotrophy created by the first mutation.

The insertion caused by the cointegration of pKEK13 into the chromosomal DNA of strain 14028 [glnH1::pGP704 (Amp$^R$)], discussed above, was moved by P22-mediated transduction into strain KK27 (ΔglnA1), discussed previously, to form strain KK45 (ΔglnA1; glnH1::pGP704).

The insertion caused by the cointegration of pKEK14 into the chromosomal DNA of strain 14028 [glnQ1::pGP704 (Amp$^R$)], discussed above, was moved by P22-mediated transduction into strain KK27 (ΔglnA1), discussed previously to form strain KK50 (ΔglnA1; glnQ1::pGP704). All transductants were purified free from phage on green plates supplemented with 2 mM glutamine. The efficacy of these avirulent microbial strains as vaccines will be discussed below.

Example 2

This example describes the construction of non-virulent or avirulent microbial strains according to the second embodiment of the present invention having at least two mutations, wherein the first mutation creates an auxotroph by blocking a gene that encodes a functional enzyme that is indispensably needed for a particular step in a biosynthetic pathway which produces a necessary nutrient, and the second mutation or mutations block a coding sequence whose product is involved with the regulation of the coding sequences that expresses a high-affinity binding or transport protein which is required to complement the auxotrophy created by the first mutation.

Tn10 insertions in the nitrogen regulatory genes were introduced into strain 14028 to form strains KK1 (ntrA209::Tn10), and KK2 (ntrC352::Tn10) as discussed above. Strains KK1 and KK2 were then used as donor strains for P22-mediated transduction into strain KK27 (ΔglnA1), discussed previously, to form strains KK30 (ΔglnA1; ntrA209::Tn10), and KK34 (ntrC352::Tn10), respectively. As discussed previously, KK4 [μglnA1-ntrC) 60; zig214::Tn10] was also constructed. The efficacy of these avirulent microbial strains as vaccines will be discussed below.

Mouse Virulence Assays

Virulent properties of all the various *S. typhimurium* strains constructed, as described above, were tested by intraperitoneal or oral inoculations of female BALB/c mice and the results are presented in Table 1.

TABLE 1

Bacterial Strains and their properties

| Strain | Genotype | I.P. $LD_{50}$ | Oral $LD_{50}$ | Competitive Index (I.P.)[a] |
|---|---|---|---|---|
| KK14 | "wildtype" zig214::Tn10 | <10 | <5.0 × 10$^6$ | 0.8070 |
| KK1 | ntrA209::Tn10 | <10 | <5.0 × 106 | 0.0087 |
| KK2 | ntrC352::Tn10 | <10 | | 1.2700 |
| KK10 | ntrB137::Tn10 | <10 | | 1.0210 |
| KK27 | ΔglnA1 | <10 | | 1.0710 |
| KK44 | glnH1::pGP704 | <10 | | 1.3780 |
| KK49 | glnQ1::pGP704 | <10 | | 0.8020 |
| KK4 | Δ(glnA-ntrC)60; zig214::Tn10 | >5.0 × 10$^5$ | >1.8 × 10$^9$ | <0.0001 |
| KK30 | ΔglnA1; ntrA209::Tn10 | >5.0 × 10$^5$ | | 0.0028 |
| KK34 | ΔglnA1; ntrC352::Tn10 | >5.0 × 10$^5$ | | <0.0001 |
| KK45 | ΔglnA1; glnH1::pGP704 | >5.0 × 10$^5$ | >1.5 × 10$^9$ | <0.0001 |
| KK50 | ΔglnA1; glnQ1::pGP704 | >5.0 × 10$^5$ | | <0.0001 |

[a]Defined as the ratio of output mutant strain:wild-type divided by the ratio of input mutant strain:wild-type strain. Two mice for each strain were inoculated intraperitoneally with a mixture of mutant and wild-type strains. The approximate amount of input bacteria were 500 mutant:500 wild-type (1:1) for strains KK1, KK10, KK14, KK27, KK44, and KK49; and 5000 mutants:50 wild-type (100:1) for strains KK4, KK30, KK34, KK45 and KK50. When mice were moribund, spleens were isolated, homogenized, and plated for CFUs. 100 CFUs of input and output bacteria were scored for the antibiotic marker or Gln phenotype contained in each mutant strain. Values for output are the average of two mice.

Female BALB/c mice were purchased from Charles River Breeding Laboratories, Inc., (Wilmington, Mass.) and were 6 to 8 weeks of age at initial challenge. *S. typhimurium* strains were grown overnight at 37° C. to stationary phase in Luria Broth (LB) supplemented with 2 mM glutamine. Bacteria were washed once with PBS, then diluted in PBS to the approximate appropriate dilution (samples were plated for colony forming units (CFUs) on LB supplemented with 2 mM glutamine to give an accurate bacterial count). Mice were challenged with 100 μl bacterial dilutions either intraperitoneally or perorally; for peroral inoculations bacteria were washed and concentrated by centrifugation, the bacteria were then resuspended in 0.1M NaHCO$_3$, to neutralize stomach acid, and administered as a 0.1 ml bolus to animals under ether anesthesia. For all $LD_{50}$ determinations, 5 mice each were inoculated per dilution. Control mice received PBS only.

The data represented in Table 1 demonstrates that it is not sufficient alone to block either a biosynthetic pathway causing an absolute requirement for a nutrient which is normally available in the host to be vaccinated, or the expression of a high-affinity transport coding sequence or genes. Strain KK27 (ΔglnA1) having a non-polar chromosomal deletion in glnA had an intraperitoneal $LD_{50}$ of less than ten bacteria, similar to the wild-type strain (KK14), as did the strains having Tn10 insertions in ntrA (KK1), ntrB(KK10), ntrC (KK2), or pGP704 insertions in glnH (KK44), and glnQ (KK49). However, strains having at least two mutations as taught by the present invention are attenuated. Strain KK4 [Δ(glnA1-ntrC) 60] having an operon deletion in glnA ntrBC had an I.P. $LD_{50}$ of greater than 10$^5$ bacteria and oral $LD_{50}$ of greater than 10$^9$ bacteria (oral $LD_{50}$ of wild-type strains is approximately 10$^5$ bacteria). Strains with the non-polar ΔglnA deletion combined with ntrA::Tn10 (KK30), ntrC::Tn10 (KK34), glnH::pGP704 (KK45), and glnQ::pGP704 (KK50) are similarly attenuated.

These data of the virulent properties of the non-polar (ΔglnA1) strain KK27 demonstrate that the environment(s) within the mouse encountered by *S. typhimurium* during pathogenesis contain glutamine in sufficient concentrations to compliment the auxotrophy, and that the ntr system or its target gene the glnHPQ operon is required to compensate for the inability of the bacterium to synthesize glutamine.

Competition Assays:

For in vivo competition studies, bacteria were treated as discussed above, then mutant cells were mixed with wild-type cells at a 1:1 or 100:1 ratio (approximate input bacteria was 500 mutant+500 wild-type, or 5000 mutant+50 wild-type). Actual ratios were determined by first plating input bacteria on LB+2 mM glutamine, then scoring one hundred colonies for tetracycline, or ampicillin resistance or glutamine auxotrophy. Bacteria were injected intraperitoneally, then after 4–5 days, when mice appeared moribund, they were sacrificed and their spleens isolated, homogenized, diluted and plated. Again, the ratio of mutant to wild-type was determined by scoring one hundred colonies for the mutant phenotype. The competitive index essentially reflects how fit the mutant strain is compared to the wild-type strain. Thus, those strains that display a competitive index of less than 0.0001 reflect the fact that no mutant strains were recovered from the spleens. Consequently, the mice died as a result of the wild-type strains.

The competitive index is just an additional indicator for how fit the mutant strains are compared to wild-type; but it does not necessarily have a direct correlation with full virulence. For example, strain KK1 has an $LD_{50}$ which is the same as wild-type, however, the competitive index appears to be low, that is 0.0087. Observation of mice infected with strain KK1 shows that it takes the KK1 strain approximately twice as long to kill the mice as compared to wild-type. Therefore, given enough time strain KK1 will appear in the spleen at higher levels.

Protective efficacy of attenuated strains:

Strains which demonstrated attenuation as a result of intraperitoneal or oral challenges of BALB/c mice were further tested for protective immunity against subsequent challenge by the wild-type strain at 10$^5$ I.P. or 10$^9$ orally. After four weeks, surviving mice were challenged with the wild-type 14028 strain as noted in Table 2, below. Survival for four weeks post challenge was deemed full protection. These data, presented in Table 2, demonstrate the potential use of the present invention in developing vaccine strains.

TABLE 2

Virulence and protective efficacy of Salmonella strains

| Strain | Immunizing Dose | Initial Survivors/total | Wildtype Challenge $1.5 \times 10^5$(I.P.) | Wildtype Challenge $10^9$(oral) |
|---|---|---|---|---|
| none | | 10/10 | 0/5 | 0/5 |
| KK4 | 15 | 5/5 | 5/5 | |
| Δ(glnA-ntrC)60; | $1.6 \times 10^2$ | 5/5 | 5/5 | |
| zig214::Tn10 | $1.6 \times 10^3$ | 5/5 | 5/5 | |
| | $7.0 \times 10^3$ | 4/4 | 4/4 | |
| | $1.6 \times 10^4$ | 5/5 | 5/5 | |
| | $1.6 \times 10^3$ | 10/10 | 5/5 | 5/5 |
| | $1.8 \times 10^{9(oral)}$ | 9/10 | 4/4 | 5/5 |
| KK30 | 10 | 5/5 | 5/5 | |
| ΔglnA1; | $1.5 \times 10^5$ | 4/4 | 4/4 | |
| ntrA209::Tn10 | | | | |
| KK34 | 10 | 4/5 | 2/4 | |
| ΔglnA1; | $1.5 \times 10^5$ | 4/5 | 4/4 | |
| ntrC352::Tn10 | | | | |
| KK45 | 10 | 5/5 | 0/5 | |
| ΔglnA1; | $1.5 \times 10^2$ | 5/5 | 5/5 | |
| glnH1::pGP704 | $1.5 \times 10^3$ | 5/5 | 5/5 | |
| | $1.5 \times 10^4$ | 5/5 | 5/5 | |
| | $1.5 \times 10^5$ | 5/5 | 5/5 | |
| | $1.5 \times 10^{9(oral)}$ | 5/5 | 5/5 | |
| KK50 | 10 | 5/5 | 1/5 | |
| ΔglnA1; | $1.5 \times 10^5$ | 4/5 | 4/4 | |
| glnQ1::pGP704 | | | | |

These data demonstrate that pathogenic microorganisms can be attenuated and used as live vaccines by introducing at least two mutations into the pathogen's chromosomal DNA that result in an auxotrophy for a nutrient available within the host and the inability to complement the auxotrophy through expression of a specific transport system. Strain KK4 which contains a single deletion disabling the glnA gene as well as the ntrB and ntrC genes, performs exceptionally well at immunizing the vaccinated host against a challenge by corresponding wild-type pathogen. Strains such as KK45 and KK50 also show promise for the use as live vaccines; however, the immunizing dose requirement is slightly higher. This is most likely a result of being more highly attenuated so that there is a lower survival rate within the host. Therefore, when a low immunizing dose, such as ten bacteria are administered those bacteria do not survive within the vaccinated host for a period of time sufficient to elicit a immunogenic response prior to their death within the vaccinated host. Whereas, with larger immunizing doses there is a greater likelihood that some attenuated pathogens will survive long enough within the vaccinated host to provoke a strong immunogenic response.

The Salmonella cells of the present invention are useful sources of immunological protection against human disease such as gastroenteritis due to *S. typhimurium*. Introduction of identical or similar mutations into other Salmonella species should produce vaccines to protect against additional disease that affects animals (for example, e.g., *S. enteritidis*) or humans (e.g., *S. typhi*). Additionally, it is anticipated that bacterial cells of the present invention other than Salmonella, such as *mycobacterium tuberculosis*, and *H. pylori* may be attenuated. In particular, cells of the present invention may be prepared and used as the basis of a live vaccine capable of colonizing the inoculated animal's intestine and provoking a strong immune reaction including a secretory IgA response.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be restored to falling within the scope of the invention as defined by the claims which follow.

DEPOSITS

The following deposits were made on Apr. 11, 1995, with the American Type Culture Collection (ATCC), where the deposits were given the following accession numbers:

| Deposit | Accession No. |
|---|---|
| *S. typhimurium* KK4 | 55665 |
| *S. typhimurium* KK27 | 55666 |
| *S. typhimurium* KK44 | 55667 |
| *S. typhimurium* KK49 | 55668 |

Applicants' assignee, President and Fellows of Harvard College, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. 1.14 and 35 U.S.C. 122. The deposited material will be maintained with all the care necessary to keep it viable and uncontaminated for a period of at least five (5) years after the most recent request for the furnishing of a sample of the deposited microorgansims, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

The embodiments of the invention in which an exclusive property or privilege is claimed are defined as follows:

1. A method for preparing an attenuated microorganism capable of provoking an immunological response by a vertebrate host susceptible to disease caused by a corresponding pathogenic microorganism comprising:

creating at least two mutations in said pathogenic microorganism wherein a first mutation results in an auxotrophic mutant which requires for proliferation, a nutrient which is available in the host tissues in an amount required for said auxotrophic mutant to proliferate, and a second mutation results in the inability of said auxotrophic mutant to specifically transport said nutrient available in the host tissues into said auxotrophic mutant; and selecting for said attenuated microorganism.

2. The method of claim 1, wherein said first mutation is introduced into a first coding sequence that expresses a functional enzyme which is indispensably required for a particular step in a biosynthetic pathway.

3. The method of claim 1, wherein said second mutation is introduced into a second coding sequence the expression of which enables said auxotroph to specifically transport said nutrient present in the host tissues into said auxotroph.

4. The method of claim 1, wherein said second mutation is introduced into a second coding sequence the expression of which is involved in the initiation of transcription at a third coding sequence, wherein said third coding sequence enables said auxotroph to specifically transport said nutrient present in the host tissues into said auxotroph.

5. The method of claim 2, wherein said biosynthetic pathway is an amino acid pathway.

6. The method of claim 5, wherein said biosynthetic pathway is a glutamine pathway.

7. The method of claim 2, wherein said first coding sequence is under nitrogen control.

8. The method of claim 7, wherein said first coding sequence is glnA and encodes glutamine synthetase.

9. The method of claim 3, wherein said second coding sequence comprises a glnHPQ operon.

10. The method of claim 9, wherein said second coding sequence is a glnH gene.

11. The method of claim 9, wherein said second coding sequence is a glnQ gene.

12. The method of claim 4, wherein said second coding sequence is under nitrogen control.

13. The method of claim 12, wherein said second coding sequence comprises a glnA ntrBC operon.

14. The method of claim 13, wherein said second coding sequence is an ntrC gene.

15. The method of claim 4, wherein said second coding sequence is an ntrA gene.

16. The method of claim 1, wherein said mutations are non-revertible.

17. The method of claim 16, wherein said mutations comprise an insertion.

18. The method of claim 16, wherein said mutations comprise a deletion.

19. The method of claim 1, including the step of introducing an expression cassette comprising structural genes of species other than the live, non-virulent vaccine, wherein said structural genes encode antigens which provoke a multiple immunogenic response from the host to be vaccinated.

20. The method of claim 19, wherein said expression cassette is operatively linked to a promoter region under nitrogen control.

21. The method of claim 1, wherein said corresponding virulent pathogenic microorganism is Salmonella.

22. The method of claim 21, wherein said Salmonella is of the species *typhimurium*.

23. A method for preparing an attenuated microorganism capable of provoking an immunological response by a vertebrate host susceptible to disease caused by a pathogenic microorganism comprising:

creating at least two mutations in the pathogenic microorganism wherein a) a first non-attenuating mutation is introduced into a first coding sequence to produce an auxotrophic mutant of said pathogenic microorganism, wherein said first coding sequence encodes an enzyme which is indispensably required for the production of a nutrient that is available in the host tissue in an amount required for said auxotroph to proliferate, and b) a second non-attenuating mutation is introduced into a second coding sequence of said pathogenic microorganism, wherein said second mutation disables a specific transport system for said nutrient into said auxotrophic mutant; and selecting for a double mutant of said pathogenic microorganism having both first and second mutations, wherein said double mutant is an attenuated microorganism.

24. The method of claim 23, wherein said second mutation is introduced into a second coding sequence the expression of which enables said auxotroph to specifically transport said nutrient present in the host tissue into said auxotroph.

25. The method of claim 23, wherein said second mutation is introduced into a second coding sequence the expression of which is involved in the initiation of transcription at a third coding sequence, wherein said third coding sequence enables said auxotroph to specifically transport said nutrient present in the host tissue into said auxotroph.

26. The method of claim 23, wherein said first coding sequence is under nitrogen control.

27. The method of claim 26, wherein said first coding sequence encodes glutamine synthetase.

28. The method of claim 24, wherein said second coding sequence comprises a glnA ntrBC operon.

29. A method for preparing an attenuated microorganism capable of provoking an immunological response by a vertebrate host susceptible to disease caused by a corresponding pathogenic microorganism comprising:

mutating a first and second coding sequence of said pathogenic microorganism, wherein a first coding sequence encodes glutamine synthetase and said second coding sequence regulates transport of glutamine synthetase into the pathogenic microorganism, wherein neither one of said mutations, independently of one another, causes attenuation of the pathogenic microorganism, and wherein attenuation is attributable to a combination of said mutations; and selecting for said attenuated microorganism.

30. The method of claim 29, wherein said second coding sequence comprises ntrA and ntrC.

31. The method of claim 29, wherein said second coding sequence encodes NTRC.

32. The method of claim 29, wherein said second coding sequence encodes NTRA.

33. A method for preparing an attenuated microorganism capable of provoking an immunological response by a vertebrate host susceptible to disease caused by the corresponding pathogenic microorganism comprising:

introducing a mutation into a glnA gene; and introducing a mutation into a glnH or glnQ gene.

34. A vaccine for provoking an immunological response in a host to be vaccinated comprising:

an auxotrophic bacterial cell of a pathogenic strain having a mutation in a coding sequence, wherein said mutation prevents said auxotrophic bacterial cell from complementing its auxotrophy when introduced into the host.

35. The vaccine of claim 34, wherein said coding sequence regulates transcription of a transporter system necessary for the complementation of said auxotrophy.

36. The vaccine of claim 34, wherein said coding sequence expresses a protein or proteins involved in the transport of a nutrient present in the host which complements said auxotrophic bacterial cell.

37. The vaccine of claim 34, wherein said auxotrophic bacterial cell requires glutamine.

38. The vaccine of claim 35, wherein said coding sequence is an ntrA gene.

39. The vaccine of claim 35, wherein said coding sequence is an ntrC gene.

40. The vaccine of claim 36, wherein said coding sequence is a glnHPQ operon.

41. The vaccine of claim 40, wherein said coding sequence is a glnH gene.

42. The vaccine of claim 40, wherein said coding sequence is a glnQ gene.

43. A vaccine for provoking an immunological response in a host to be vaccinated comprising:
   an auxotrophic pathogenic microorganism having a first non-attenuating mutation in a first coding sequence that expresses an enzyme which is indispensably required for the production of a nutrient that is available in the host in an amount required for proliferation of the auxotrophic microorganism; and
   a second non-attenuating mutation in said auxotrophic microorganism which inhibits the expression of a second coding sequence that encodes a protein involved in the transport of said nutrient.

44. The vaccine of claim 43, wherein said first coding sequence is regulated by nitrogen.

45. The vaccine of claim 44, wherein said first coding sequence encodes glutamine systhetase.

46. The vaccine of claim 43, wherein said second mutation is located in a third coding sequence the product of which regulates the transcription of said second coding sequence.

47. The vaccine of claim 46, wherein said third coding sequence is an ntrA gene.

48. The vaccine of claim 46, wherein said third coding sequence is an ntrC gene.

49. The vaccine of claim 43, wherein said second mutation is located in said second coding sequence.

50. The vaccine of claim 49, wherein said second coding sequence comprises a glnHPQ operon.

51. The vaccine of claim 49, wherein said second coding sequence is a glnH gene.

52. The vaccine of claim 49, wherein said second coding sequence is a glnQ gene.

53. A method for attenuating a pathogenic microorganism, comprising:
   creating a first mutation in a first gene of said microorganism to produce an auxotrophic mutant of said pathogenic microorganism, wherein said auxotrophic mutant requires a nutrient for growth;
   creating a second mutation in a second gene of said pathogenic microorganism, wherein said second mutation affects the expression of a component of a high-affinity transport system for said nutrient into said pathogenic microorganism; and
   wherein said first and second mutations, independently of one another, do not cause attenuation, and wherein the attenuating is attributable to a combination of said first and second mutations.

54. A vaccine comprising a pharmaceutically acceptable excipient and, as active ingredient, an attenuated form of a pathogenic microorganism, wherein attenuation is attributable to a combination of mutations, wherein a first mutation produces an auxotrophic mutant which requires a nutrient to proliferate, and wherein a second mutation disables a specific transport system for said nutrient into said microorganism.

55. The vaccine of claim 54, wherein said first mutation is in a gene encoding an enzyme in a biosynthetic pathway.

56. The vaccine of claim 55, wherein said enzyme is glutamine synthetase.

57. The vaccine of claim 54, wherein said second mutation is in a gene selected from the group glnH, glnQ, and glnP.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 28 base pairs -continued

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GCGGATCCTT YGTNCCNTTY GARTTYAA                                           28

(2) INFORMATION FOR SEQ ID NO:2:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

GCGGAATTCA RYTCCATRTA NGCRTTRTC                                          29

(2) INFORMATION FOR SEQ ID NO:3:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GCGGAATTCC GGNATGGTNT TYCARCARTT                                         30

(2) INFORMATION FOR SEQ ID NO:4:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GGCGAAGCTT ACYTGNGGRT TNCCRTCYTC                                         30
```